(12) United States Patent
Jahns et al.

(10) Patent No.: US 9,439,838 B2
(45) Date of Patent: Sep. 13, 2016

(54) COLOURING SOLUTION FOR SELECTIVELY TREATING THE SURFACE OF DENTAL CERAMIC AND RELATED METHODS

(75) Inventors: Michael Jahns, Gilching (DE); Philipp Doebert, Seefeld (DE); Holger Hauptmann, Sindelsdorf (DE); Grit Kindler, München (DE)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 14/237,207

(22) PCT Filed: Jul. 27, 2012

(86) PCT No.: PCT/US2012/048491
§ 371 (c)(1),
(2), (4) Date: Feb. 6, 2014

(87) PCT Pub. No.: WO2013/022612
PCT Pub. Date: Feb. 14, 2013

(65) Prior Publication Data
US 2014/0178834 A1    Jun. 26, 2014

(30) Foreign Application Priority Data

Aug. 11, 2011 (EP) .................................... 11177189
Mar. 5, 2012 (EP) .................................... 12158057

(51) Int. Cl.
*A61C 13/08* (2006.01)
*C04B 41/00* (2006.01)
(Continued)

(52) U.S. Cl.
CPC ......... *A61K 6/0058* (2013.01); *A61C 13/0006* (2013.01); *A61K 6/0017* (2013.01); *A61K 6/0094* (2013.01); *A61K 6/06* (2013.01); *C04B 41/009* (2013.01); *C04B 41/49* (2013.01); *C04B 41/5007* (2013.01); *C04B 41/62* (2013.01); *C04B 41/85* (2013.01); *C04B 2111/00836* (2013.01); *C04B 2111/82* (2013.01); *C04B 2201/10* (2013.01); *Y10T 428/24926* (2015.01)

(58) Field of Classification Search
CPC .................................................... A61C 13/082
USPC ................................................ 427/2.26, 2.29
See application file for complete search history.

(56) References Cited

U.S. PATENT DOCUMENTS 2,920,390 A * 1/1960 Saffir ..................... A61C 13/09
                                                              433/203.1
6,709,694 B1 * 3/2004 Suttor et al. ................. 427/2.26
(Continued)

FOREIGN PATENT DOCUMENTS

DE        19619168       10/1997
EP        1961719        8/2008
(Continued)

OTHER PUBLICATIONS

International Search Report for PCT International Application No. PCT/US2012/048491 mailed on Oct. 25, 2012, 3 pages.

*Primary Examiner* — Cachet Sellman

(57) ABSTRACT

The invention relates to a solution to be selectively applied to individual parts of the surface of dental ceramic(s) and a process for using the solution in the dental field. More specifically the invention relates to a solution comprising a) a solvent, b) an effect agent, and c) a complexing agent. The invention also relates to a kit comprising the solution and to a method of using the solution for selectively treating of parts of the surface dental ceramic(s). The invention also relates to a application instrument suitable for applying the solution.

12 Claims, 4 Drawing Sheets

(51) Int. Cl.
*A61K 6/00* (2006.01)
*A61K 6/06* (2006.01)
*C04B 41/85* (2006.01)
*C04B 41/49* (2006.01)
*C04B 41/50* (2006.01)
*C04B 41/62* (2006.01)
*A61C 13/00* (2006.01)
*C04B 111/00* (2006.01)
*C04B 111/82* (2006.01)

(56) References Cited

U.S. PATENT DOCUMENTS 6,756,421 B1    6/2004  Todo

2007/0062410 A1* 3/2007 Thiel et al. ............... 106/31.05
2010/0260924 A1* 10/2010 Karim et al. ............... 427/2.26

FOREIGN PATENT DOCUMENTS

| | | |
|---|---|---|
| EP | 1961719 A1 * | 8/2008 |
| ES | 2238938 | 9/2005 |
| WO | WO 00-04618 | 1/2000 |
| WO | WO 00-46168 | 8/2000 |
| WO | WO 2004-110959 | 12/2004 |
| WO | WO 2005-082811 | 9/2005 |
| WO | WO 2008-098157 | 8/2008 |
| WO | WO 2009-014903 | 1/2009 |

* cited by examiner

COLOURING SOLUTION FOR SELECTIVELY TREATING THE SURFACE OF DENTAL CERAMIC AND RELATED METHODS

CROSS REFERENCE TO RELATED APPLICATIONS

This application is a national stage filing under 35 U.S.C. 371 of PCT/US2012/048491, filed Jul. 27, 2012, which claims priority to European Application No. 11177189.5 filed Aug. 11, 2011 and which claims priority to European Application No. 12158057.5 filed Mar. 5, 2012, the disclosures of which are incorporated by reference in their entirety herein.

FIELD OF THE INVENTION

The invention relates to a solution to be selectively applied to individual parts of the surface of dental ceramic(s) and a process for using the solution in the dental field. More specifically the invention relates to a solution comprising a) a solvent, b) an effect agent, and c) a complexing agent. The invention also relates to an application instrument useful for applying the solution.

BACKGROUND OF THE INVENTION

A dental ceramic can either be coloured by incorporating pigments into the ceramic material or using metal salts containing solutions which are to be applied on the surface of partially sintered dental ceramic with the aim to colour the dental ceramic in its entirety.

In this respect DE 196 19 168 A1 describes a ceramic colouring solution consisting essentially of water and a palladium containing compound dissolved therein. The solution might further contain co-solvents such as alcohols, glycols, glycol ether or polyethylene glycol.

WO 2004/110959 relates to a colouring solution for ceramic framework. The solution comprises a solvent (e.g. water), a metal salt and polyethylene glycol having a Mn in the range of 1.000 to 200.000.

WO 00/46168 A1 (corresponding to U.S. Pat. No. 6,709, 694 B1) refers to colouring ceramics by way of ionic or complex-containing solutions containing defined concentrations of at least one salts or complexes of the rare earth elements or of the elements of the subgroups. The solution might contain additives like stabilizers, complex builders, pigments and beating additives.

WO 2008/098157 relates to a colouring solution for dental ceramic framework comprising a solvent, a colouring agent comprising metal ions, and a complexing agent, wherein the amount of complexing agent is sufficient to dissolve the colouring agent in the solvent.

WO 2009/014903 relates to a colouring solution for dental ceramic articles, the solution comprising a solvent and a colouring agent comprising rare earth element ions being present in the solution in an amount of at least about 0.05 mol/l solvent and transisition ions being present in the solution in an amount of about 0.00001 to about 0.05 mol/l solvent.

The present invention is intended to improve the known colouring solutions and to extend its use.

SUMMARY OF THE INVENTION

It would be desirable to have a solution or composition, which can be used to selectively treating specific parts of the surface of pre-sintered dental ceramic.

Moreover, it would be desirable if this can be done without a complete diffusion of the composition into the pores of the pre-sintered dental ceramic so that a defined application of the colouring solution can be accomplished.

At least one of these objects can be achieve by providing a non-water based solution for selectively applying parts of the surface of a dental ceramic, the solution comprising
  a solvent being miscible with water but not being water,
  an effect agent comprising metal ions, the effect caused by the effect agent being either colouring, providing fluorescence or a combination thereof,
  a complexing agent being able to form a complex with the metal ions of the effect agent, wherein the complex is soluble in the solvent.

The invention also relates to a process of selectively treating parts of the surface of a dental ceramic comprising the steps of
  a) providing the solution as described in the present text and a dental ceramic having an outer surface,
  b) applying the solution described in the present text to only a part of the outer surface of the dental ceramic,
  c) optionally drying the dental ceramic, and
  d) optionally firing the dental ceramic.

In another aspect, the invention relates to a dental ceramic framework treated with the colouring solution or obtainable by the process described in the present text.

In a further aspect, the invention relates to the use of a colouring solution as described in the present text for selectively colouring the outer surface of a dental ceramic framework.

In a further aspect the invention relates to a kit of parts comprising at least one receptacle containing the solution as described in the present text, a receptacle containing the solvent as described in the present text and optionally application and mixing appliances.

The invention is also directed to a pen comprising the non-water based solution and a kit of parts comprising at least two pens, each pen comprising a non-water based solution with a different colour.

Definitions

Unless defined differently, for this description the following terms shall have the given meaning:

A "solvent" is any solvent which is able to dissolve the effect agent. The solvent should be sufficiently chemically stable if combined with the effect agent and/or complexing agent. That is, the solvent shall not be decomposed by the other components present in the composition.

"Soluble" means that a component (solid) can be completely dissolved within a solvent. That is, the substance is able to form individual molecules (like glucose) or ions (like sodium chloride) when dispersed in water at 23° C. The solution process, however, might take some time, e.g. stirring the composition over a couple of hours (e.g. 10 or 20 h) might be required.

More specifically, according to the invention a substance or composition is defined as "soluble", if less than about 10 wt.-% or less than about 5 wt.-% or less than about 2 wt.-% or less than about 1 wt-% or less than about 0.1 wt.-% (with respect to the whole composition) of solid substance remains after the following procedure:
  a. 800 mg of substance and 8.0 g of solvent are placed into a centrifuge test tube of known weight.
  b. The test tube is closed and shaken for 60 minutes.
  c. The mixture is centrifuged with centrifugal acceleration (ac) of 9870 m/s$^2$ for 20 min.
  d. The supernatant liquid is decanted.
  e. The precipitate is re-suspended with 6 g solvent.

f. The test tube is shaken for 60 min, centrifuged as described above, and the supernatant liquid decanted again.
g. Steps e) and f) are repeated one time.
h. The remaining precipitate is calcined for 12 h at 500° C. (+/−3.5° C.).
i. After cooling to room temperature the dry weight of the sample is determined and used for calculating the soluble fraction.

A substance or composition is defined as "insoluble", if more than about 90 wt.-% or more than about 50 wt.-% or more than about 25 wt.-% or more than about 10 wt.-% (with respect to the whole composition) of substance remains unsolved after the procedure described above.

The term "water-miscible" or "miscible with water" means that a certain liquid is miscible with water at 23° C. at least to a high extend to provide a homogeneous solution, i.e. without phase separation. More specifically, the water-miscible liquid is defined as miscible with water if at least 10 g or at least 100 g or at least 500 g or at least 750 g or least 1000 g water-miscible liquid is soluble in 1000 g water without phase separation. Ideally, no phase separation occurs at ambient conditions independent from the mixing ratio (e.g. ethanol is miscible with water in all ratios).

The term "amount sufficient to dissolve" describes the amount of an agent needed to fully dissolve a certain substance in a certain solvent so that a storage stable composition can be obtained. The time needed to dissolve a substance is not particularly limited, however, the dissolution should occur within a reasonable time (e.g. within about 10 to about 48 h) using common equipment like mechanical stirrers and heaters.

A solution can be classified as "storage stable", if it remains stable over a considerable long period of time (at least about 4 weeks to more than about 12 months under ambient conditions). A storage stable solution typically does not show any visible (visible to the human eye) precipitation of the colouring agent during storage at ambient conditions (about 23° C., about 1013 mbar) and does not show decomposition of the solution or precipitation of single or multiple components.

"Non-water based" means that the major part (at least more than about 50 or more than about 60 or more than about 70 or more than about 80 or more than about 90 wt.-%) of the liquid components being present in the composition or solution is/are components being different from water.

An "effect agent" is any agent, which is able to a) lead to a colour change, b) provide fluorescence, or c) provide a combination of either of these effects to a dental ceramic either right after treatment of the ceramic with the effect agent or after a firing step of the treated ceramic.

A "complexing agent" is any agent which is able to form complexes with the colouring agent.

A "complex", also known as coordination compound, in chemistry usually is used to describe molecules or ensembles formed by the combination of ligands and metal ions. Originally, a complex implied a reversible association of molecules, atoms, or ions through weak chemical bonds. As applied to coordination chemistry, this meaning has evolved. Some metal complexes are formed virtually irreversibly and many are bound together by bonds that are quite strong.

The ions or molecules surrounding the metal are called ligands. Ligands are generally bound to a metal ion by a coordinative bonding (donating electrons from a lone electron pair to the Lewis acidic metal center), and are thus said to be coordinated to the ion. Those ligands are referred to as "coordinating ligands".

The term "component A is used in an at least stoichiometric ratio with respect to component B" means that components A and B are used in an at least equimolar amount with respect to each other. That is, the addition of a larger molar amount of component A compared to component B is not excluded.

Rare earth elements and/or of the subgroups of the rare earth elements include Ce, Pr, Nd, Sm, Eu, Gd, Tb, Dy, Ho, Er, Tm, Yb and Lu.

Transition metals comprise the metals listed in the columns of the Periodic Table of Elements starting with the elements Sc, Ti, V, Cr, Mn, Fe, Co, Ni, Cu and Zn and the metals listed below those elements.

Metals of the main groups comprise the metals listed in the main groups of the Periodic Table of Elements starting with the elements Li, Be, B, C, N, O, F and the metals listed below those elements.

A "particle" means a substance being a solid having a shape which can be geometrically determined Particles can typically be analysed with respect to e.g. grain size.

The mean particle size of a powder can be obtained from the cumulative curve of the grain size distribution and is defined as the arithmetic average of the measured grain sizes of a certain powder mixture. Respective measurements can be done using commercially available granulometers (e.g. CILAS Laser Diffraction Particle Size Analysis Instrument).

The term "dental ceramic" is to be understood as any ceramic which can be used in the dental field. In this respect, the dental ceramic shall have sufficient strength. Examples include inlays, onlays, crowns, abutments and bridges (including 2 parts, 3 parts, 4 parts, 5 parts or 6 parts bridges). The dental ceramic has usually a 3-dimensional inner and outer surface including convex and concave structures. Compared to other ceramic such as pottery or paving stones, the dental ceramic is small and filigree. The thickness of the dental ceramic can vary from very thin, e.g. at the edges and rims (below about 0.1 mm) to considerably thick, e.g. in the biting area (up to about 7 mm) Typically, the dental ceramic of the invention comprises or essentially consists of a polycrystalline ceramic material comprising $Al_2O_3$ or Yttrium stabilized $ZrO_2$.

A dental ceramic is classified as "pre-sintered" if the dental ceramic framework has been treated with heat (temperature range from about 900 to about 1100° C.) for about 1 to about 3 h to such an extent that the raw breaking resistance of the dental ceramic framework measured according to the "punch on three ball test" ISO 6872 is within a range of about 15 to about 55 MPa or about 30 to about 50 MPa. A presintered dental ceramic framework usually has a porous structure and its density (usually 3.0 g/cm$^3$ for an Yttrium stabilized $ZrO_2$ ceramic) is less compared to a completely sintered dental ceramic framework (usually 6.1 g/cm$^3$ for an Yttrium stabilized $ZrO_2$ ceramic).

A dental ceramic is classified as "absorbent" if the dental ceramic is able to absorb a certain amount of a solvent, comparable to a sponge. The amount of solvent which can be absorbed depends e.g. on the chemical nature of the dental ceramic framework, the viscosity of the solvent, the porosity and pore volume of the dental ceramic.

A dental ceramic can be characterized as "homogeneously coloured", if no colour spots can be identified with the human eye on the surface of the dental ceramic after the sintering process. More precisely, this can be proven e.g. using a commercially available Hunter Lab System or the system GretagMacbeth Color i7. If desired, the homogeneity can be measured according to DIN 5033 Measurement of Colours; Parts 1-8 (Normvalenz-System, L*a*b*-Farbraum nach CIE, 1976); DIN 6174 Farbmetrische Bestimmung von Farbabständen bei Körperfarben nach der CIE-LAB-Formel; DIN 55981 (ISO 787-25) Farbabstandsbestimmung ΔE* using standard operating procedures according to the manufacturer's operation manual (Hunter Lab., Corp.) to determine the sample dimension, the calibration and measure procedure. Further hints to this measuring system can also be found in DE 100 52 203 A1 on page 3, line 56 to page 4, line 6 (corresponding to U.S. Pat. No. 6,756,421, column 4, lines 26 to 55).

By "machining" is meant milling, grinding, cutting, carving, or shaping a material by a machine. Milling is usually faster and more cost effective than grinding.

"Sintering" means making objects from a powder, by heating the material (typically below its melting point-solid state sintering) until its particles adhere to each other.

"Glass and/or glass ceramic material" means that the material comprises either a glass material alone or that the material comprises a glass material and a ceramic material in a combination or mixture.

A "powder" means a dry, bulk solid composed of a large number of very fine particles that may flow freely when shaken or tilted.

"Density" means the ratio of mass to volume of an object. The unit of density is typically $g/cm^3$. The density of an object can be calculated e.g. by determining its volume (e.g. by calculation or applying the Archimedes principle or method) and measuring its mass.

"Ambient conditions" mean the conditions which the inventive solution is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are adjusted to about 23° C. and about 1013 mbar.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Figure 1:
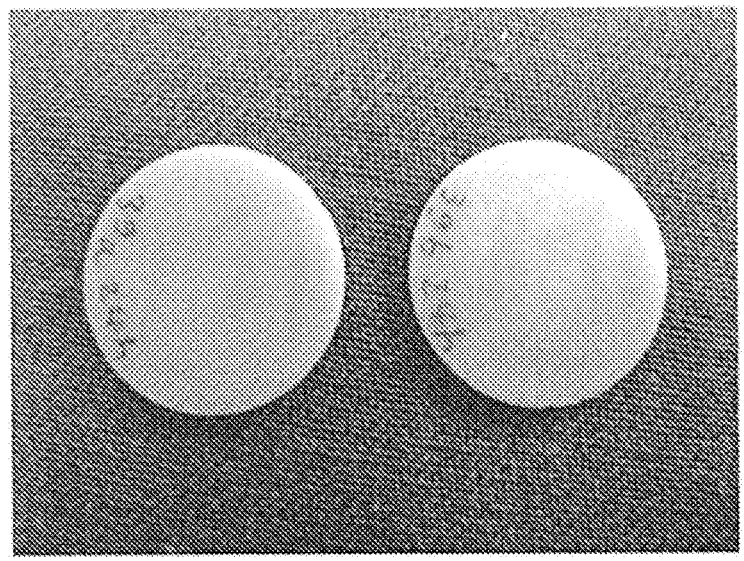
FIG. 1 shows sintered zirconia discs painted with inventive composition. Left: painted in dry state; right: painted in wet state (infiltrated with de-ionized water).

In the dental field, water-based colouring liquids are commonly used for colouring especially zirconia based dental ceramic frameworks for dental restorations in a pre-sintered stage. This is typically achieved by dipping the framework into a colouring solution in its entirety. By doing so, a homogenous colour of the whole dental ceramic is usually achieved.

However, if individual colouration in small defined areas is desired, the water-based liquids of the prior art cannot be used because the different colours typically will mix up and diffuse into parts of the ceramic article where they are not supposed to be present.

The inventive solution or composition solves this problem by allowing a dental technician to selectively apply a colour or produce another effect to the surface of a dental ceramic e.g. using a brush.

It was found that the colour or other effect remains on the spot or area of the surface where the solution has been applied to and does typically not diffuse through the rest of the material of the dental ceramic.

Thus, the invention enables the local and specific application of a colour or effect to selective parts of the surface of a ceramic material. It allows an exact colouration of individual parts of the surface of a dental ceramic.

The solution is typically applied to the surface of pre-sintered, porous dental ceramic. The painted features remain essentially sharp even if the bulk of the dental ceramic is still wet from a prior colouring step.

Thus, the inventive solution can also be applied to wetted dental ceramics, which have already been coloured by using a commercially available water-based colouring liquid, without the risk of the colour spreading indiscriminately due to diffusion.

On the other hand the inventive composition is also compatible with water-based colouring liquids in the sense that application of the composition will not affect the subjacent "background colour" of the dental ceramic having already been treated with a water-based colouring liquid in an undesired manner.

If desired, the colour impression produced by the composition in the material can be further adjusted by diluting the composition with a dilution liquid or solvent.

Without wishing to be bound to a particular theory, a possible explanation for this finding is as follows:

If the composition is applied to a dry, porous material, it will migrate into the pores of the material. But this happens only to a very limited extent, mainly due to the comparably high viscosity of the composition. If the composition, however, is applied to a water-soaked, porous material, the water-soluble solvent will mix with the water already present inside the pores of the ceramic material. The chromophore, however, which is not as readily miscible with water, will remain in the portion of the material, where it has been applied to, due to its low solubility in the water being present in the pores.

Thus, by mixing a water-insoluble chromophore or a chromophore which has only a limited water-solubility with a solvent, which is able to take up the chromophore, but still remains miscible with water, the above mentioned object can be achieved.

The inventive solution can be used as so-called "effect colours" for selectively colouring the surface of dental ceramic(s), especially of wetted pre-sintered dental ceramic(s).

Moreover, it was found that the inventive solution(s) remain stable over a considerable long period of time. They typically do not show any visible precipitation of the effect agent during storage at ambient conditions (23° C., normal pressure).

Other embodiments, features and advantages of the present invention will be apparent from the following detailed description, drawings, and claims.

DETAILED DESCRIPTION

The inventive solution typically has an adequate viscosity so that a sufficient amount of solution can be applied to the surface of the dental ceramic.

According to one embodiment, the solution has a viscosity above about 100 or above about 200 or above about 500 or above about 1,000 mPa*s (measured at 23° C. with a shear rate of 50 s$^{-1}$). The viscosity of the solution is typically below about 15,000 or below about 10,000 or below about 8,000 mPa*s (measured at 23° C. with a shear rate of 50 s$^{-1}$).

Typical viscosity ranges include from about 100 to about 15,000 or from about 500 to about 10000 or from about 1000 to about 8,000 mPa*s (measured at 23° C. with a shear rate of 50 s$^{-1}$).

If the viscosity of the colouring solution is too high, the effect agent might not enter the pores of the ceramic material at all. On the other hand, if the viscosity of the solution is too low, the effect agent might diffuse through the pores too much.

If desired, the measurement of the viscosity can be done as follows: A viscosimeter MCR300 (from Anton Paar Comp.) is used. A portion of the composition is placed between two steel discs with a diameter of 8 mm and a gap of 1 mm at a temperature of 23° C. The gap is filled completely with the composition. Excess composition is removed. The shear rate between the rotating discs d(gamma)/dt is set constantly to 50 s$^{-1}$. The measurement is done 500 s after starting the shearing process of the composition.

If dissolved in water, the solution typically has a pH-value in the range of between about 2 to about 10 or 3 to 9 or 4 to 8.

The pH-value of the solution is not particularly limited. Examples of useful pH-values are equal or greater than 2 or 3 or 4 or 5 or 6 or 7 or 8 or 9. Thus, the pH-value can be in a range of about 2 to about 10 or in the range of about 3 to about 9. Measurement of the pH-value can be achieved by means known by the person skilled in art. E.g. an instrument like Metrohm™ 826 or pH indicator paper can be used.

In a preferred embodiment the inventive solution is transparent.

A solution can be characterized as transparent within the meaning of the invention if a beam of visible light (about 400 to about 700 nm) is not scattered by the solution and cannot be observed by side view (no Tyndal effect). However, the intensity of the penetrating beam of visible light in direction of the beam may be weakened due to absorption of the light by the colouring metal ions.

The solution is a non-water based solution.

The solution is used for being selectively applied to parts of the surface of a dental ceramic. That is, the solution is only applied to parts of the surface of the dental ceramic but usually not to the whole surface. In contrast to commercially available colouring liquids, the dental ceramic is not dipped completely into the inventive solution.

Moreover, the solution cannot only be applied to dry surfaces of dental ceramics, but also to wetted dental ceramics, especially to pre-sintered dental ceramics.

The solution comprises a solvent. The solvent is miscible with water. The solvent, however, is not water.

Typically, the solvent can be characterized by at least one of the following features:

molecular weight (Mw): from about 30 to about 1,000 g/mol or from about 60 to about 400 g/mol;

viscosity: from about 1 to about 2000 mPa*s or from about 100 to about 1,500 mPa*s (measured at 23° C. at a shear rate of 50 s-1);

free of polymerizable groups like (meth)acrylate groups, epoxy groups, carbon-carbon unsaturated groups;

not containing elements like S, P.

Mw (substance) is the average molecular weight of the respective polymer used.

Solvents which can be used include polyalcohols including ethylene glycol, polyethylene glycols, glycerol and mixtures thereof.

Polyethylene glycols which can be used can be represented by formula (1)

$$R1O-(CH2-CH2-O)m-R1 \qquad (1)$$

with R1=H, Acyl, Alkyl, Aryl, Alkylaryl, Polypropylglycol, Poly-THF, preferably H, Acetyl, Methyl, Ethyl, Propyl, Butyl, Hexyl, Octyl, Nonyl, Decyl, Lauryl, Tridecyl, Myristyl, Palmityl, Stearyl, Oleyl, Allyl, Phenyl, p-Alkylphenyl, Polypropyleneglycol, Poly-THF and m=about 2 to about 100, preferably about 2 to about 20, more preferably about 2 to about 5

The average molecular weight (Mw) of the polyethylene glycol should be in the range of about 100 to about 5.000, preferably in the range of about 100 to about 1.000, more preferably in the range of about 100 to about 300.

If desired, the average molecular weight (Mw) can be determined according to procedures known to a person skilled in the art as described for example in Arndt/Müller, Polymercharakterisierung, Hanse Verlag, 1996. Depending on the molecular weight to be determined, it might be necessary to apply different measurement methods (see below).

Most PEGs (polyethylene glycols) include molecules with a distribution of molecular weights, i.e. they are polydisperse. The size distribution can be characterized statistically by its weight average molecular weight (Mw) and its number average molecular weight (Mn), the ratio of which is called the polydispersity index (Mw/Mn). Mw and Mn can be measured by mass spectroscopy.

Specific examples of water-miscible liquid, which can be used, include polyol(s) (including polyvinyl alcohol), glycol ether(s) (e,g, PEG 200, PEG 400, PEG 600, diethylene glycol methyl ether, diethylene glycol ethyl ether), alcohol(s) (including 1,2-propanediol, 1,3-propanediol, ethanol, (n- and iso-)propanol, glycerol), glycerol ether, and mixtures thereof.

In particular, the following solvents were found to be useful: glycerol, ethylene glycol, propylene glycol and mixtures thereof.

The solvent should be able to dissolve the effect agent together with the complexing agent. Dissolving means that the solution does not contain particles being visible to the human eye.

The solution is essentially free of water.

Essentially free of water means that the composition does not contain water, which has been willfully added as a solvent. However, traces of water being present in the composition due to the components used are acceptable. Thus, this term includes that water might be present up to an amount of about 10 wt.-% or up to about 7 wt.-% or up to about 5 wt.-% or up to about 2 wt.-% or up to about 1 wt.-% with respect to the whole solution or composition, respectively.

If too much water is present in or added to the solution, the viscosity of the solution is too low. This may impede the precise application of the solution to the surface of the porous dental ceramic(s).

The amount of solvent used is not particularly limited unless the result to be achieved cannot be obtained.

The solvent is typically used in an amount of at least about 40 or at least about 70 or at least about 80 wt.-% with respect to the whole weight of the solution.

There is no particular upper amount, however, the solvent is typically used up to an amount of up to about 99 or up to about 96 or up to about 90 wt.-% with respect to the whole weight of the solution.

Useful ranges for the solvent include from about 40 to about 98 wt.-% or from about 70 to about 96 wt.-% or from about 80 to about 90 wt.-% with respect to the whole weight of the solution.

The solution also comprises an effect agent. The effect agent comprises metal ions.

The effect agent provides either colour or fluorescent properties or provides a combination of colouring and fluorescent properties.

Examples of effect agents include salts of rare earth elements and/or salts of transition metals and/or salts of metals of the main groups.

Metals of the main groups include the metals listed in the main groups of the Periodic Table of Elements having the numbers 1, 2, 13, 14, 15, 16; IUPAC classification new. Transition metals include those of the groups 3, 4, 5, 6, 7, 8, 9, 10, 11 and 12 of the Periodic Table of Elements; IUPAC classification new.

Rare earth elements or metals include those classified as Lanthanides in the Periodic Table of Elements. Examples include Ce, Pr, Nd, Sm, Eu, Gd, Tb, Dy, Ho, Er, Tm, Yb and Lu.

Metals which were found to be especially useful for the purpose of the invention include Fe, Mn, Er, Pr, Co and Bi. The metals can be used either alone or in admixture with other metals.

The effect agent is typically used as a salt comprising metal cations and anions, wherein the anions are selected from the group consisting of $NO_3^-$, $NO_2^-$, $CO_3^{2-}$, $HCO_3^-$, $ONC^-$, halogen anions (fluoride, chloride, bromide), acetates and mixtures thereof.

As described in more detail below, the complexing agent can be added as a separate component. However, it is also feasible that the complexing agent is at least partially identical with the anion of the effect agent, or that the anion of the effect agent can be classified as complexing agent as well.

Examples for these kinds of anions include gluturate, lactate, gluconate, propionate, butyrate, glucuronate, benzoate, phenolate, citrate, salicylate, glycinate, acetylacetonate, propylendiamine, ascorbate and others.

The amount of effect agent used is not particularly limited unless the result to be achieved cannot be obtained. The metal ions are contained in the solution in an amount sufficient to achieve an adequate effect of the surface of the dental ceramic.

Good results can be achieved e.g. with amounts (calculated with respect to the metal) in the range of about 0.02 to about 20% by weight of effect agent or in the range of about 0.1 to about 10% by weight, or in the range of about 0.2 to about 6% by weight or in the range of about 0.2 to about 4% by weight with respect to the weight of the whole composition.

If the amount of effect agent used is too low, the effects obtained in the ceramic might be too weak for the intended use.

If the amount of effect agent used is too high, it can be difficult to produce a solution. So, there might remain particles within the composition, which can cause undesired shading effects on the surface of the dental ceramic.

The solution also comprises a complexing agent. The complexing agent is able to form a complex with the metal ions of the effect agent. The complex formed is soluble in the solvent. Typically the complex formed is better soluble in the solvent than in water. According to a particular embodiment, the complex formed is essentially insoluble in water.

Typically, the complexing agent is present in the solution in an amount sufficient to dissolve the effect agent in the solvent or to prevent precipitation of the effect agent.

The complexing agent can be present in an amount of at least about 1 wt.-% or at least about 5 wt.-% or at least about 10 wt.-% with respect to the amount of the whole composition. There is no upper limit, however, usually the amount of complexing agent used does not exceed an amount of about 50 wt.-% or about 40 wt.-% or about 30 wt.-% with respect to the amount of the whole composition.

E.g., the complexing agent can be used in an at least stoichiometric ratio with respect to the molar amount of the ions contained in the effect agent.

Good results can be achieved, if the ratio of molar amount of complexing agent to the molar amount of metal ion being present in the effect agent is equal to or greater than about 1 or about 2 or about 3.

If the amount of complexing agent used is too low, the effect agent might not be dissolved entirely.

If the amount of complexing agent used is too high, the excess complexing agent itself might remain unsolved.

The complexing agent is usually added as a separate component of the composition. However, it can also be added as part of the effect agent, e.g. as counter ion to the metal ion being present in the effect agent. Examples include citrate and acetylacetonate.

Without wishing to be bound by any theory, it is assumed that the complexing agent is able to form a complex with the metal ion(s) of the effect agent assisting the effect agent in dissolving in the chosen solvent and preventing the effect agent from precipitating from the solution especially during storage.

The increased stability of a chelated complex is called the chelate effect. In this respect, the complexing agent can also be characterized as a chelating agent (or a polydentate ligand), which can bond to more than one coordination site on the central atom. Because it is necessary to break all of the bonds to the central atom for the ligand to be completely displaced, it requires more energy to increase the number of separate molecules. If a chelate were replaced by several monodentate ligands (such as water or ammonia), the total number of molecules would decrease, whereas if several monodentate ligands were replaced by a chelate, the number of free molecules increases. The effect is therefore entropic in that more sites are used by less ligands and this leaves more unbonded molecules: a total increase in the number of molecules in solution and a corresponding increase in entropy.

According to the present invention the complexing agents can be classified as follows:

Complexing agents with 6 coordinating ligands include EDTA (ethylene diamine tetra acetic acid); 18-crown-6; 2,2,2-crypatand; polymeric ligands like poly acrylate, poly asparagate, acidic peptides with an "infinite" number of coordinating ligands are counted as complexing agents with 6 coordinating ligands.

Complexing agents with 5 coordinating ligands include 15-crown-5; cyclo-pentadien.

Complexing agents with 4 coordinating ligands include NTA (nitrilotriacetate); 12-crown-4; triethylentetramine; porphin$^{2-}$; phthalocyanin$^{2-}$bis(salicilate)ethylenbis(imin)salen$^{2-}$.

Complexing agents with 3 coordinating ligands include $C_3H_5O(COO)_3^{3-}$.

Complexing agents with 2 coordinating ligands include $HC_6H_5O_7^{2-}$; salicylate, glycinate; lactate; acetylacetonate; propylendiamine; ascorbate $C_6H_6O_6^{2-}$; $C_3H_5O(COOH)(COO)_2^{2-}$.

A citrate is an ionic form of citric acid, such as $C_3H_5O(COO)_3^{3}$, that is, citric acid minus three hydrogen ions. Citrates are compounds containing this group, either ionic compounds, the salts, or analogous covalent compounds, esters. Since citric acid is a tribasic acid, intermediate ions exist, hydrogen citrate ion, $HC_6H_5O_7^{2-}$ and dihydrogen citrate ion, $H_2C_6H_5O_7^-$. These may form salts as well, called acid salts. Salts of the hydrogen citrate ions are weakly acidic, while salts of the citrate ion itself (with an inert cation such as sodium ion) are weakly basic.

Complexing agents having anionic groups as complexing ligands can be preferred. At least parts of the complexing ligands should be anionic. Complexing agents having only uncharged complexing ligands (or even cationic ligands) like pure amines (e.g. ethylendiamin at pH values at 8 to 14) might not yield sufficiently stable solutions.

The inventive solution may also contain one or more additive(s).

Additives which can be added to the solution include stabilizers (such as methoxy phenol hydrochinone, Topanol A, ascorbic acid and mixtures thereof), buffers (such as acetate or amino buffers and mixtures thereof), preservative agents (such as sorbic acid or benzoic acid and mixtures thereof), soluble colourants (e.g. colourants which can be added to food) and mixtures thereof.

There is no need for additive(s) to be present, however, if they are present, they are typically present in an amount which is not detrimental to the purpose to be achieved when applying the solution.

If additive(s) are present, they are typically present in an amount of about 0.01 to about 10 wt.-% or from about 0.05 to about 5 wt.-% or from about 0.1 to about 3 wt.-% with respect to the whole solution.

According to a further embodiment, the solution comprises the components in the following amount:
  the solvent in an amount of about 40 to about 98 wt.-% or from about 70 to about 95 wt.-%,
  a effect agent comprising metal ions in an amount of about 0.02 to about 20 wt.-% or from about 0.1 to about 15 wt.-% (calculated with respect to the amount of metal),
  a complexing agent in an amount of about 1 to about 50 wt.-%, or from about 5 to about 40 wt.-%, and
  optionally additives in an amount of about 0.01 to about 10 wt.-% or from about 0.05 to about 5 wt.-%,
wt.-% with respect to the whole composition.

The solution of the present invention is typically applied the surface of pre-sintered ceramic bodies of various compositions, especially such comprising or preferably consisting essentially of $ZrO_2$ and/or $Al_2O_3$, respectively.

The term "consisting essentially of" means that the major part (e.g. greater than about 80 or about 85 or about 90 wt.-%) of the dental ceramic is based on either $ZrO_2$ or $Al_2O_3$ or a mixture of these oxides. The rest of may be comprised of oxides selected from $HfO_2$ and stabilizers including $Y_2O_3$, CaO, MgO, $CeO_2$ or mixtures thereof.

These compositions are known to the skilled person in the art (examples of useful compositions are described e.g. in WO 00/4618 A1).

According to a preferred embodiment, the dental ceramic is a $ZrO_2$ based ceramic and is preferably stabilized with $Y_2O_3$. The dental ceramic is in a pre-sintered stage.

Yttrium doped tetragonal stabilized zirconia is sometimes also referred to as YTZP and commercially available from e.g. Tosoh Comp., Japan.

The inventive solution or composition can be produced by mixing its components. This can be done at room temperature or by applying heat and/or while stirring.

Applying heat and/or stirring can be beneficial in order to accelerate the dissolution process of the effect agent into the solvent.

The composition is stirred until the effect agent and the complexing agent are completely dissolved in the solvent.

If desired, additives (like those mentioned above) can be added.

The invention is also directed to a process of selectively treating parts of the surface of a dental ceramic. This process typically comprises the steps of
  providing the solution as described in the present text and a dental ceramic having an outer surface,
  applying the solution as described in the present text to only a part of the outer surface of the dental ceramic, especially the surface of a pre-sintered dental ceramic.
  optionally drying the dental ceramic, and
  optionally firing the dental ceramic.

The dental ceramic is typically in a pre-sintered stage. A dental ceramic being in a pre-sintered stage has usually open pores and thus can be described as absorbent.

Selectively applying the solution to the surface of the dental ceramic is usually achieved by painting e.g. using a brush. However, the solution can also be applied by using a sponge or fabric or by spraying.

Drying the coloured dental ceramic is not absolute necessary, but can be preferred to reduce the time needed for firing and to avoid undesired in-homogenous colour effects. Drying can be effected by simply storing the dental ceramic e.g. on a plate at ambient conditions for a couple of hours (about 1 to about 3 h). If, however, a high boiling solvent is used, drying might be difficult to achieve.

The firing conditions are dependent on the ceramic material used. A furnace which can be used is the commercially available LAVA™ Therm (3M ESPE). During the firing process the coloured dental ceramic is sintered to its final shape, thereby undergoing changes with regard to dimension, density, hardness, raw breaking resistance and/or grain size.

The firing usually takes place for a $ZrO_2$ based ceramic at a temperature above about 1300° C., preferably above about 1400° C., more preferably above about 1450° C. and lasts for at least about 0.5 h, preferably for at least about 1 h, more preferably for at least about 2 h.

For an $Al_2O_3$ based ceramic the firing usually takes place at a temperature above about 1350° C., preferably above about 1450° C., more preferably above about 1650° C. and lasts for at least about 0.5 h, preferably for at least about 1 h, more preferably for at least about 2 h.

The dental ceramic onto which the solution is applied can be dry or wet.

"Wet" means that the ceramic material still contains a small amount of water. However, there should be no visible spots of water residues on the surface.

A pre-sintered or porous material sample is considered wet, if the material has been completely dipped into water for about 10 s, removed from the water and wrapped for about 10 s into a paper tissue being able to absorb water or alternatively, if a water-based solution has been applied to large areas of the material using e.g. a sponge, a brush, etc.

The surface of a pre-sintered or porous material sample is considered dry, if the material has been completely dipped into a water-based solution for about 10 s, removed from the water, wrapped for about 10 s into a paper tissue being able to absorb water and placed into an oven for about 1 h at a temperature of about 200° C. or left to dry open to the air for about 4 h, or if no water-based solution has been applied to the pre-sintered ceramic at all.

The invention is also related to a dental ceramic obtainable by a process as described in the present text. A dental ceramic having being treated according to the above described process steps is different from dental ceramics which have been treated with water-based colouring solutions. Applying water-based colouring solutions to the surface of dental ceramics typically leads to diffuse colouring of the whole dental ceramic, whereas the inventive solution allows for a more accurate, well defined colouring.

If desired, the extent of diffusion of the solution on the surface of the treated dental ceramic can be determined as follows: The width of a line drawn with the inventive composition can be visually confirmed after sintering. More accurately, X-ray fluorescence (XRF) measurements can be conducted in micro mapping mode to determine the line's width, i.e. scanning the surface of the ceramic in e.g. 0.25 mm steps and measuring only small spots of e.g. about 0.5 mm diameter.

A width of e.g. about 0.5 mm of the drawn structures is considered to meet the expectations of a dental technician in most cases for an effect agent being applied to only selective parts of the surface of a dental ceramic.

The dental ceramic can have the shape of a crown, inlay, onlay, abutment or bridge.

The invention is also directed to the use of a solution as described in the present text for selectively treating parts of the surface of a dental ceramic, especially the surface of pre-sintered dental ceramic(s) in dry but also in wet stage.

According to a further embodiment, the invention is directed to a kit of parts comprising
at least one receptacle containing the solution as described in the present text;
a receptacle containing the solvent as described in the present text; and
optionally application and mixing appliances.

Examples of receptacles include bottles, wells, tubes and vessels.

A typical example of a kit according to the invention includes about 2 to 10 receptacles containing solutions as described in the present text, each differing from the others by its content and/or concentration of metal ions.

The solvent being provided in a separate receptacle enables the practitioner to further individualize the solutions, especially with respect to intensity.

Examples of application appliances include brushes, sponges, (hollow) needles, pens etc.

Examples of mixing appliances include mixing wells, trays, plates, slides, etc.

According to one embodiment the composition is applied to the surface of dental ceramic(s) with a pen, the pen comprising a housing, a brush tip, a removable cap and a reservoir for storing the non-water based solution described in the present text.

The brush tip is typically attached or fixed to the front end of the housing. The reservoir is typically fixed or attached to the rear end of the housing. The removable cap is typically used for protecting the brush tip during storage.

Using a pen may facilitate the application of the non-water based solution and will help the practitioner to save time.

Currently, colouring solutions are usually offered in bottles and are applied to porous ceramics with a separate brush or even by dipping the entire ceramic into the colouring solution. This often goes along with a lot of waste of the colouring solution. By using a pen, there will be essentially no waste of the colouring solution.

Further, a pen with a cap will prevent the pen from drying out if not used.

Providing individual pens for individual colouring solutions may further facilitate the application of the composition to the surface of porous dental ceramic(s). Until now, usually only one brush is used and that brush has to be cleaned thoroughly before a further colouring solution is applied.

If, however, one pen for one colour is provided, switching the colours during the application process is quite easy and more save for the dental technician, while mixing of different colours using this kind of equipment is still possible by subsequent application of different colours to the ceramic surface.

The volume of the reservoir may be in a range from about 1 ml to about 10 ml or from about 2 ml to about 5 ml.

The reservoir may be removable or fixed to the housing of the pen.

According to one embodiment, the reservoir is exchangeable. The exchangeable reservoir may have the shape of a cartridge or bullet.

The brush tip typically comprises bristles. The material the bristles are made of can be selected from artificial or natural materials. Artificial materials include polyamides (nylon), polyesters and mixtures thereof. Natural materials usually include different kinds of animal hair. The brush tip may be removable or exchangeable, too.

The length of the brush tip extending from the pen is typically within a range from about 5 to about 20 mm or from about 8 to about 15 mm. If the bristles are too short, application of the solution to the inside of a dental restoration may be difficult. If, on the other hand, the bristles are loo long, the handling of the brush itself might become impractical for dental applications.

The thickness of the brush tip at its base is typically in the range from about 0.3 to about 5 mm or from about 1 to about 4 mm. If the tip is too broad, application of the solution to the inside of a dental restoration may be difficult. If, on the other hand, the tip is too narrow, the handling of the brush itself might become impractical for dental applications.

Furthermore, if the length and the thickness of the brush tip is either too low or too high, it will be difficult to apply the non-water based solution properly, that is either too little or too much of the non-water based solution is applied. Both may be detrimental for achieving an accurately coloured dental ceramic.

The shape of the brush tip should be tapered and fan out, if desired, when pressure is applied. Thus, the brush tip should have a some flexibility. A brush tip with these properties can be used to draw thin lines and also to paint on larger areas.

A combination of a brush tip comprising bristles having a length from about 8 to about 15 mm with the non-water based solution described in the present text having a viscosity above about 200 mPa*s or above about 500 mPa*s (measured at 23° C.) was found to be beneficial. Such a combination facilitates the accurate application of the non-water based solution on the surface of the porous dental ceramic(s).

Thus, the invention is also directed to a pen as described in the present text comprising the non-water based solution.

According to another embodiment the invention is related to kit of parts comprising at least two pens, each pen comprising a housing, a brush tip, a removable cap and a reservoir for storing the non-water based solution described in the present text, wherein the non-water based solutions stored in the reservoir differ from each other with respect to the colour.

Depending on the variety of colours desired, the kit may comprise at least 2, 3, 4, 5 pens. A typical kit of parts may comprise up to 20 or up to 10 pens.

The invention also relates to reservoirs or containers containing the non-water based solution described in the present text, wherein the reservoirs are adapted to be placed in a pen comprising a housing, a removable cap and a brush tip.

The solution of the invention does typically not contain components which might produce a toxic, injurious, or immunological response in living tissue or components or additives which jeopardize the intended purpose to be achieved with the present invention, especially in the sintered ceramic.

Thus, for examples components or additives added in an amount which finally (e.g. after a sintering step) results in a non-tooth-coloured article are usually not contained in the final dental restoration. Typically, an article is characterized as tooth coloured if it can be allocated a colour from the Vita™ colour code system, known to the person skilled in the art.

The colouring solution does typically also not comprise insoluble pigments or insoluble additives or thickening agents, like methyl cellulose, silica (e.g. Aerosil) etc.

Moreover, if possible, the colouring solution should not or only contain a small amount of ingredients which can be detrimental to the firing equipment during the sintering process.

According to a specific embodiment, the inventive solution does not contain reactive monomers (i.e. chemically reactive moieties like double bonds, e.g. (meth)acrylates. Thus, the composition does not exhibit chemical reactivity under ambient conditions, i.e. components being present in the composition do not react with each other at ambient conditions.

According to a further embodiment, the inventive solution does not contain glass or glass/ceramic particles.

The complete disclosures of the patents, patent documents, and publications cited herein are incorporated by reference in their entirety as if each were individually incorporated.

The following examples are given to illustrate, but not limit, the scope of this invention.

EXAMPLES

Unless otherwise indicated, all parts and percentages are on a weight basis, all water is deionized water, and all molecular weights are weight average molecular weight. Moreover, unless otherwise indicated all experiments were conducted at ambient conditions (23° C.; 1013 mbar).

Inventive Example 1

5.0 g of glycerol were mixed with 0.2 g of praseodymium (III) acetylacetonate by stirring for about 2 h. This step was performed under vacuum to avoid the inclusion of air bubbles into the viscous liquid. The composition was left for about 24 h before using it for painting of zirconia samples.

The composition was applied to a dry and to a wetted disc of porous pre-sintered zirconia. The wetted disc was prepared by dipping a dry disc into de-ionized water for a few seconds. The disc was then left to dry for a few minutes. For the painting process, there should be no free liquid from the soaking step remaining on the disc's surface, since the painting liquid would spread indiscriminately.

Thin and thick lines were painted onto the surfaces. After that, the material was put into a furnace and sintered at 1500° C. for 2 h. As a result, white, dense zirconia discs with yellow lines on them were obtained. The lines had the same shape as they had prior to the sintering step. The color did not diffuse throughout the disc (see FIG. 1).

Inventive Example 2

5.0 g of glycerol were mixed with 0.4 g of praseodymium (III) acetylacetonate by stirring for about 2 h. This step was performed under vacuum to avoid the inclusion of air bubbles into the viscous liquid. The composition was left for about 24 h before using it for painting zirconia samples.

The composition was applied to a dry and to a wetted disc of porous pre-sintered zirconia. The wetted disc was produced by dipping a dry disc into a model coloring liquid (containing de-ionized water, triammonium citrate, poly(ethylene)glycol and a mix of praseodymium, erbium and manganese acetate) for a few seconds. The disc was then left to dry for a few minutes. For the painting process, there should be no free liquid from the soaking step remaining on the disc's surface, since the painting liquid would spread indiscriminately.

Figure 2:
FIG. 2 shows sintered zirconia discs painted with inventive composition. Left: painted in dry state; right: painted in wet state (infiltrated with colouring liquid).

Thin and thick lines were painted onto the surfaces. After that, the material was put into a furnace and sintered at 1500° C. for 2 h. As a result, dense zirconia discs with yellow lines on them were obtained. The lines had the same shape as they had prior to the sintering step. The color did not diffuse throughout the disc. The formerly dry disc had a white background color and the formerly wetted disc now has a yellowish background color, obscuring a bit the yellow painted sections (see FIG. 2).

Inventive Example 3

2.5 g of glycerol were mixed with 0.2 g of praseodymium (III) acetylacetonate by heating the mixture to 100° C. and stirring for about 1 h. As the viscosity of glycerine drops when being heated, no vacuum was necessary during this step. The light green, turbid dispersion turns into a golden-brown, clear solution. To make the painted regions visible before sintering, a caramel-based organic color was added to the composition (about 1 drop of caramel color E150D).

Figure 3:
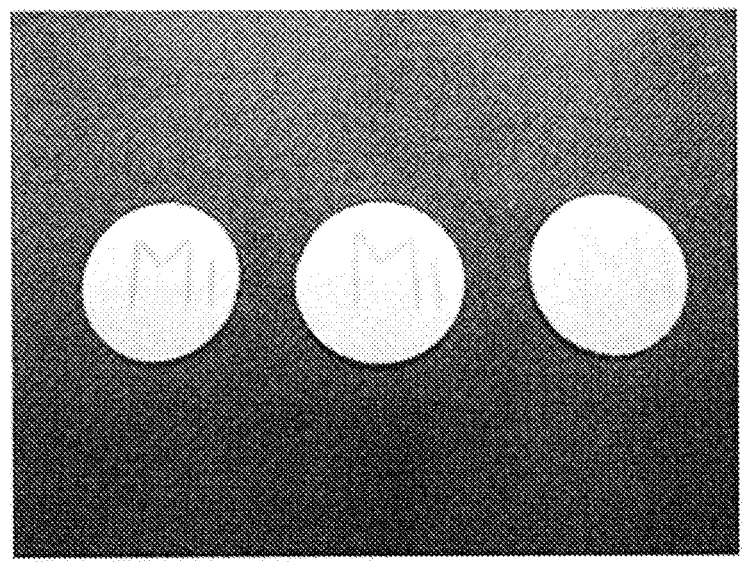
FIG. 3 shows pre-sintered zirconia discs painted with inventive composition. Left: painted in dry state; middle: painted in wet state (infiltrated with de-ionized water); right: painted in wet state (infiltrated with colouring liquid).

The composition was applied to one dry and to two wetted discs of porous pre-sintered zirconia (see FIG. 3). One of the wetted discs was produced by dipping a dry disc into de-ionized water, the other by dipping a dry disc into a model coloring liquid (containing de-ionized water, triammonium citrate, poly(ethylene)glycol and a mix of praseodymium, erbium and manganese acetate) for a few seconds. The discs were then left to dry for a few minutes. For the painting process, there should be no free liquid from the soaking step remaining on the discs' surface, since the painting liquid would spread indiscriminately.

Figure 4:
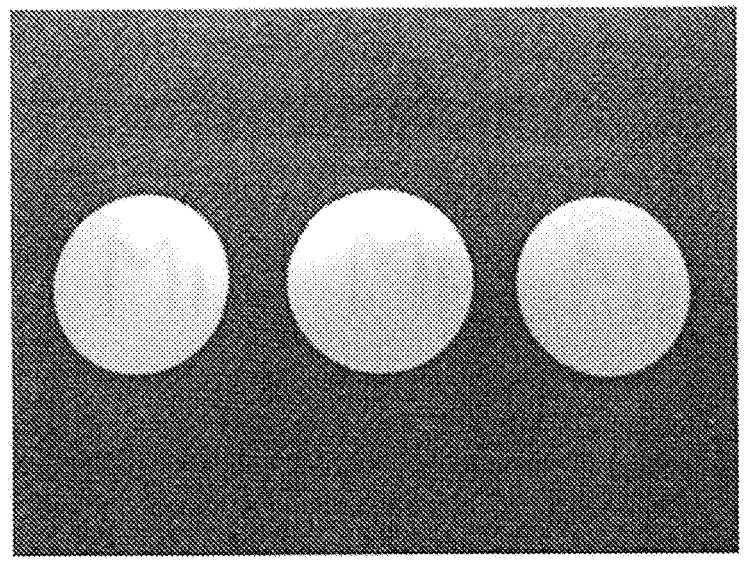
FIG. 4 shows sintered zirconia discs painted with inventive composition. Left: painted in dry state; middle: painted in wet state (infiltrated with de-ionized water); right: painted in wet stage (infiltrated with colouring liquid).

Thin and thick lines were painted onto the surfaces. After that, the material was put into a furnace and sintered at 1500° C. for 2 h. As a result, dense zirconia discs with yellow lines on them were obtained. The lines had the same shape as they had prior to the sintering step. The color did not diffuse throughout the disc. The formerly dry disc and the disc infiltrated with water have a white background color and the disc infiltrated with coloring liquid now had a yellowish background color (see FIG. 4).

Inventive Example 4

100.0 g of glycerol were mixed with 60.0 g of erbium(III) acetate and 42.0 g of triammonium citrate by heating the mixture to 50° C. and stirring for about 48 h. As the viscosity of glycerine drops when being heated, no vacuum was necessary during this step. The light red, turbid dispersion turns into a light red, clear solution. To make the painted regions visible before sintering, 3.0 g Beet Root food color were added to the composition.

The composition was applied to a dry disc of porous pre-sintered zirconia. One thin line was painted onto the surface. After that, the material was put into a furnace and sintered at 1500° C. for 2 h. As a result, a dense zirconia disc with a pink lines on it was obtained. The line had the same shape as it had prior to the sintering step. The color did not diffuse throughout the disc.

The experiment was repeated, using water instead of glycerol as solvent, for comparison. The thickness of the erbium-containing lines after sintering was measured using X-ray fluorescence in micro-mapping mode (Rigaku ZSX Primus II).

The measurement showed a line thickness of about 0.5 mm for the inventive glycerol-based solution and a line thickness of about 1.5 mm for the comparative water-based solution. In addition, the erbium concentration in the comparative sample was more than twice as high as in the inventive sample. This indicates, that the thin water-based solution has been sucked out of the brush by the porous ceramic and that there is little control of the amount brought into the material Comparative Example 1

10.0 g of de-ionized water, 0.2 g of triammonium citrate, 0.2 g of poly(ethylene)oxide (Mw=5,000,000) and 0.05 g of manganese(II) chloride were mixed by stirring for about 24 h. A highly viscous liquid was obtained.

The composition was applied to a dry and to a wetted disc of porous pre-sintered zirconia. The wetted disc was produced by dipping a dry disc into a model coloring liquid (containing de-ionized water, triammonium citrate, poly(ethylene)glycol and a mix of praseodymium, erbium and manganese acetate) for a few seconds. The discs were then left to dry for a few minutes. For the painting process, there should be no free liquid from the soaking step remaining on the disc's surface, since the painting liquid would spread indiscriminately.

Figure 5:
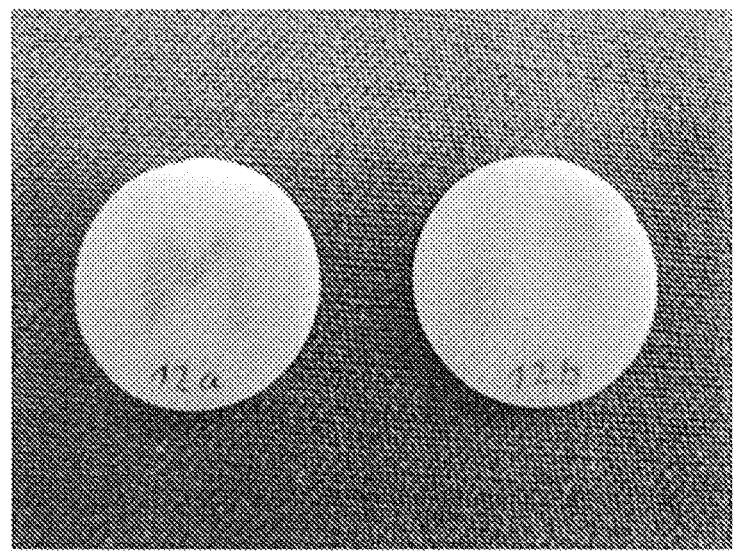
FIG. 5 shows sintered zirconia discs painted with comparative composition. Left: painted in dry state; right: painted in wet state (infiltrated with colouring liquid).

Thin and thick lines were painted onto the surfaces. After that, the material was put into a furnace and sintered at 1500° C. for 2 h. As a result, dense zirconia discs with grey lines on them were obtained. The lines on the formerly dry disc, which retained its white background color, had the same shape as they had prior to the sintering step. But the lines on the formerly wetted disc, which now had a yellowish color, are broader and have no sharp edges anymore (see FIG. 5).

Figure 6:
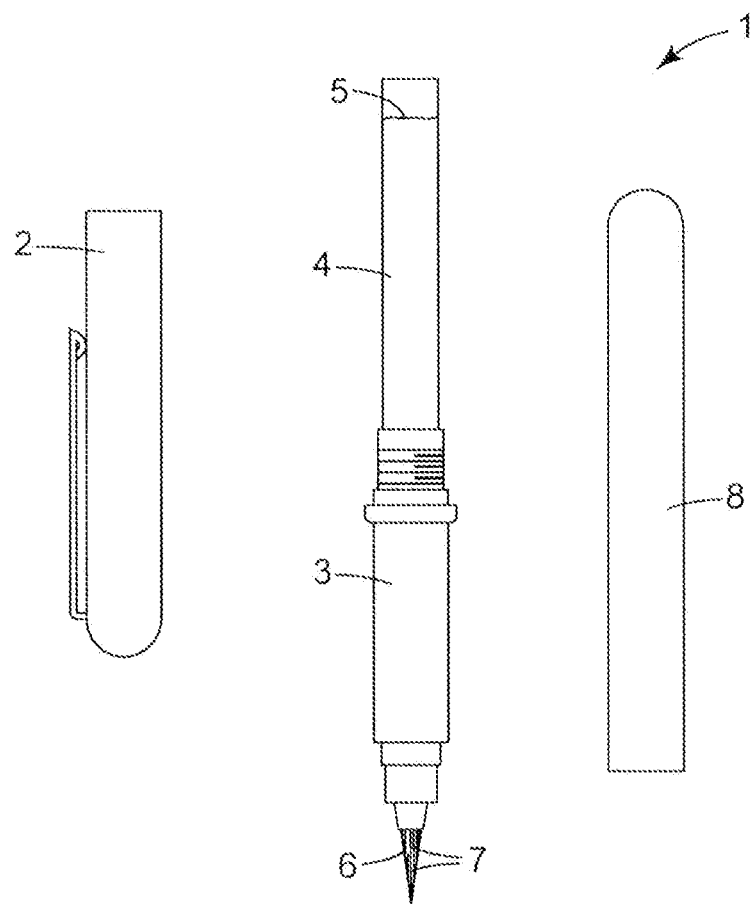
FIG. 6 shows a possible application instrument for the inventive composition.

In FIG. 6 a brush pen (1) is shown which can be used for applying the non-water based solution described in the present text. The brush pen comprises a removable cap (2), a housing (3) and a removable cartridge (4) containing the non-water based solution (5). At the top of the housing (3) there is a brush tip (6) comprising bristles (7). For better handling the removable cartridge (4) can be covered with a casing (8), if desired.

Figure 7:
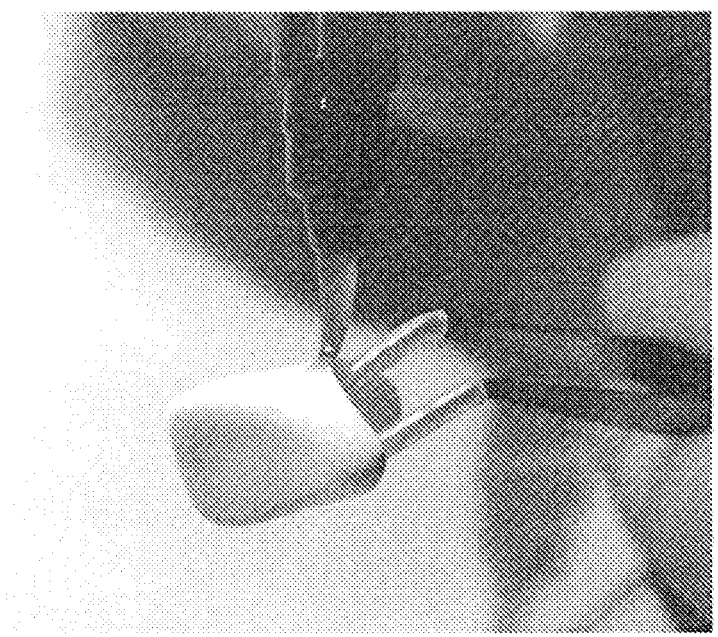
FIG. 7 shows the application of the composition to selected areas of a crown.

In FIG. 7 it is shown how the non-water based solution described in the present text is applied to selected areas of a crown.

The invention claimed is:

1. A process of selectively treating parts of the surface of a dental ceramic comprising the steps of
   a) providing a solution and a dental ceramic having an outer surface,
      wherein the solution comprises
      a solvent being miscible with water but not being water,
      an effect agent comprising metal ions, the effect caused by the effect agent being either colouring, providing fluorescence or a combination thereof,
      a complexing agent being able to form a complex with the metal ions of the effect agent,
      wherein the complex is soluble in the solvent, the solution having a viscosity above about 200 mPa*s at 23° C.,
      wherein the water-content of the solution is below about 10 wt.-% with respect to the whole composition,
   b) applying the solution to only a part of the outer surface of the dental ceramic,
   c) optionally drying the dental ceramic, and
   d) optionally firing the dental ceramic.

2. The process according to claim 1, wherein the dental ceramic comprises $ZrO_2$, $Al_2O_3$, $TiO_2$ or mixtures thereof.

3. The process according to claim 2, wherein the dental ceramic fulfills at least one of the following conditions: a) the dental ceramic is in a pre-sintered stage, b) the dental ceramic is wet.

4. A process of selectively treating parts of the surface of a dental ceramic comprising the steps of
   a) providing a solution and a dental ceramic having an outer surface,
      wherein the solution comprises
      a solvent being miscible with water but not being water and having a molecular weight from about 60 to about 1,000 g/mol,
      an effect agent comprising metal ions, the effect caused by the effect agent being either colouring, providing fluorescence or a combination thereof,
      a complexing agent being able to form a complex with the metal ions of the effect agent,
      wherein the complex is soluble in the solvent, the solution having a viscosity above about 200 mPa*s at 23° C.,
      wherein the water-content of the solution is below about 10 wt.-% with respect to the whole composition,
   b) applying the solution to only a part of the outer surface of the dental ceramic,
   c) optionally drying the dental ceramic, and
   d) optionally firing the dental ceramic.

5. The process according to claim 4, wherein the solvent comprises a polyalcohol.

6. The process according to claim 4, wherein the solvent comprises ethylene glycol, polyethylene glycols, glycerol, or mixtures thereof.

7. The process according to claim 4, wherein the solvent comprises glycerol.

8. A process of selectively treating parts of the surface of a dental ceramic comprising the steps of
a) providing a solution and a dental ceramic having an outer surface,
wherein the solution comprises
a solvent being miscible with water but not being water and having a molecular weight from about 100 to about 5,000 g/mol,
an effect agent comprising metal ions, the effect caused by the effect agent being either colouring, providing fluorescence or a combination thereof,
a complexing agent being able to form a complex with the metal ions of the effect agent,
wherein the complex is soluble in the solvent, the solution having a viscosity above about 200 mPa*s at 23° C.,
wherein the water-content of the solution is below about 10 wt.-% with respect to the whole composition,
b) applying the solution to only a part of the outer surface of the dental ceramic,
c) optionally drying the dental ceramic, and
d) optionally firing the dental ceramic.

9. The process according to claim 8, wherein the solvent comprises polyethylene glycol.

10. The process according to claim 8, wherein the polyethylene glycol is of the formula: R1O—(CH2-CH2-O)m-R1, where R1 is H, Acyl, Alkyl, Aryl, Alkylaryl, Polypropylglycol, or Poly-THF, and m is about 2 to about 100.

11. The process according to claim 10, where R1 is H, Acetyl, Methyl, Ethyl, Propyl, Butyl, Hexyl, Octyl, Nonyl, Decyl, Lauryl, Tridecyl, Myristyl, Palmityl, Stearyl, Oleyl, Allyl, Phenyl, p-Alkylphenyl, Polypropyleneglycol, or Poly-THF.

12. The process according to claim 10, where m is 2 to 20.

* * * * *

UNITED STATES PATENT AND TRADEMARK OFFICE
CERTIFICATE OF CORRECTION

PATENT NO. : 9,439,838 B2
APPLICATION NO. : 14/237207
DATED : September 13, 2016
INVENTOR(S) : Jahns et al.

Page 1 of 2

It is certified that error appears in the above-identified patent and that said Letters Patent is hereby corrected as shown below:

In the Specification

Column 1
Line 57, delete "transisition" and insert -- transition --, therefor.

Column 2
Line 58, delete "wt-%" and insert -- wt.-% --, therefor.

Column 4
Line 22, after "determined" insert -- . --.

Column 4
Line 41, after "mm)" insert -- . --.

Column 7
Line 57, delete "Tyndal" and insert -- Tyndall --, therefor.

Column 8
Line 31, after "5" insert -- . --.

Column 9
Line 57, delete "gluturate," and insert -- glutarate, --, therefor.

Column 11
Lines 12-13, delete "triethylentetramine;" and insert -- triethylenetetramine; --, therefor.

Column 11
Lines 13-14, delete "bis(salicilate)ethylenbis(imin)salen$^{2-}$" and insert
-- bis(salicylate)ethylenebis(imin)salen$^{2-}$. --, therefor.

Signed and Sealed this
Sixteenth Day of May, 2017

Michelle K. Lee
*Director of the United States Patent and Trademark Office*

CERTIFICATE OF CORRECTION (continued)
U.S. Pat. No. 9,439,838 B2

Column 11
Line 16, delete "$C_3H_8O(COO)_3^{3-}.$" and insert -- $C_3H_5O(COO)_3^{3-}.$ --, therefor.

Column 11
Line 18, delete "$HC_6H_8O_7^{2-};$" and insert -- $HC_6H_5O_7^{2-};$ --, therefor.

Column 11
Lines 21-22, delete "$C_3H_5O(COO)_3^3,$" and insert -- $C_3H_5O(COO)_3^{3-},$ --, therefor.

Column 11
Line 26, delete "$HC_6H_8O_7^{2-}$" and insert -- $HC_6H_5O_7^{2-}$ --, therefor.

Column 11
Line 27, delete "$H_2C_6H_8O_7^{-}.$" and insert -- $H_2C_6H_5O_7^{-}.$ --, therefor.

Column 11,
Line 40, delete "hydrochinone," and insert -- hydroquinone, --, therefor.

Column 12
Line 36, delete "ceramic." and insert -- ceramic, --, therefor.

Column 14
Line 53, delete "loo" and insert -- too --, therefor.

Column 17
Line 47, after "material" insert -- . --.